(12) United States Patent
Maxwell, Jr. et al.

(10) Patent No.: US 7,716,065 B1
(45) Date of Patent: May 11, 2010

(54) METHOD OF GENERATING AND MAINTAINING A PATIENT MEDICATION PROFILE

(75) Inventors: Milton B. Maxwell, Jr., Nashville, TN (US); Bradley R. Mitchell, Nashville, TN (US); Norman J. Noffsinger, Franklin, TN (US)

(73) Assignee: MAX Well Medical, Inc., Nashville, TN (US)

( * ) Notice: Subject to any disclaimer, the term of this patent is extended or adjusted under 35 U.S.C. 154(b) by 1408 days.

(21) Appl. No.: 10/686,900

(22) Filed: Oct. 16, 2003

(51) Int. Cl.
*G06Q 50/00* (2006.01)
*A61B 5/00* (2006.01)
(52) U.S. Cl. .............................. 705/2; 705/3
(58) Field of Classification Search .................. 705/2–3
See application file for complete search history.

(56) References Cited

U.S. PATENT DOCUMENTS

| | | | |
|---|---|---|---|
| 5,899,998 A | 5/1999 | McGauley | |
| 6,421,650 B1* | 7/2002 | Goetz et al. ................. | 705/3 |
| 6,988,075 B1* | 1/2006 | Hacker ........................ | 705/3 |
| 7,072,840 B1* | 7/2006 | Mayaud ...................... | 705/2 |
| 2002/0032582 A1* | 3/2002 | Feeney et al. ............... | 705/2 |
| 2002/0052760 A1* | 5/2002 | Munoz et al. ............... | 705/2 |
| 2002/0161607 A1* | 10/2002 | Subich ........................ | 705/3 |
| 2003/0061074 A1* | 3/2003 | Dutta et al. .................. | 705/4 |
| 2003/0204415 A1* | 10/2003 | Knowlton .................... | 705/2 |
| 2004/0088317 A1* | 5/2004 | Fabrick et al. .............. | 707/102 |
| 2004/0128162 A1* | 7/2004 | Schlotterbeck et al. ...... | 705/2 |
| 2004/0162835 A1* | 8/2004 | Ghouri ........................ | 707/100 |

* cited by examiner

*Primary Examiner*—C. Luke Gilligan
*Assistant Examiner*—Kristine K Rapillo
(74) *Attorney, Agent, or Firm*—Waddey & Patterson; I. C. Waddey, Jr.; Gary L. Montle (57) ABSTRACT

The present invention discloses methods for conveniently providing a complete medication profile of a patient. A medication profile report may be obtained on-line by the patient or a registered provider. In addition to information regarding the expiration of prescriptions, the patient's compliance with the prescriber's directions for usage, and the names of medications being used by a patient, the medication profile report also provides the therapeutic classes of each medication, possible drug-drug interactions, and possible side effects. Convenient access to such complete medication information is highly desirable to the patient and his or her provider.

5 Claims, 5 Drawing Sheets

METHOD OF GENERATING AND MAINTAINING A PATIENT MEDICATION PROFILE

BACKGROUND OF THE INVENTION

The present invention relates generally to a method for promptly providing complete and detailed medication information of a patient to the patient, the patient's loved ones, and/or or the patient's health care provider.

More particularly, this invention pertains to the generation of a medication profile report. The medication profile report provides detailed information regarding the characteristics of each drug used by the patient. The report also provides additional information regarding possible drug-drug interactions, possible duplicate drug therapies, possible side effects and information related to the overall medication therapy of the patient.

Currently, a health care provider relies upon the patient to provide complete and detailed information regarding the medications the patient is using. The medical condition of a patient may be compromised when inaccurate or incomplete medication information is provided. A health care provider must be made fully aware of all of the drugs a patient is using as well as of all of the possible problems associated with the interaction between the combination of all of these drugs in order to avoid harmful drug-drug interactions, duplicative medication therapy, or advise the patient of any detrimental effects of the medications currently being used.

Currently, a patient must independently identify a complete listing of the medication he or she is using. Generally, upon a visit to a health care provider, a patient must recite his or her medication history in a matter of minutes. Often, the patient may totally forget one, or several, of the medications he or she is taking. Further, for individuals with complex medication regimens, obtaining a complete and accurate list of medications from the patient may be impossible. While an individual professional will most likely have records of what he or she has prescribed for the patient, the professional, in almost all cases, will not have a complete profile on the patient unless they are confident that the patient provides them with a one hundred percent accurate review of all of the medications they are taking, including those prescribed by other professionals. Additionally, the professional has to rely upon the patient to tell them whether or not the patient is taking these drugs as they have been prescribed.

What is needed, then, is a medication profile report that is conveniently obtained by a patient or his or her provider. Such a medication profile report must be obtainable 24 hours a day and must reflect the current medication usage of the patient. This report, additionally, needs to include not only what the patient has told the health care provider that they are taking but it needs to include actual dispensing information so that the provider can have a reasonably high degree of confidence that the information contained in the medication profile is complete and up to date including information regarding dispensing and compliance data.

SUMMARY OF THE INVENTION

The present invention discloses methods of generating and maintaining a medication profile for a registered patient. Disclosed herein are the steps needed for a health care provider to register with a medication profile provider in order to obtain medication information on-line, or by other remote ways. Also disclosed are steps for to generating and maintaining medication profile reports at the request of a patient or health care provider. Methods of using the on-line medication profile are also disclosed herein.

The methods disclosed herein provide a current medication profile of a registered patient in order for a patient to obtain such medication information for personal uses. The methods disclosed herein also allow a registered health care provider to obtain medication information in order to avoid duplicative medication therapy, overdosing, unnecessary side effects, drug-drug interactions, and obtain information regarding disease drug contra indications. Having such complete medical information in the form of a medication profile report will dramatically assist a health care provider in reaching the proper medical decisions for the patient.

Accordingly, one aspect of the present invention is to provide a patient's medication profile to a remote location at the request of the patient or any third party which is authorized by the patient.

Another aspect of the present invention is to provide a patient's medication profile to a registered health care provider at a remote location in order to assist the health care provider with obtaining complete medication information in order to make a medical decision.

Still another aspect of the present invention is to provide patient medication information from different pharmaceutical distributors so that such complete and accurate medication information may be used to obtain profile information regarding drug-drug interactions, medication side effects, and duplicative medication therapy which may have a severe or moderate impact upon the patient so that a preferred medication regime and schedule can be identified.

Yet another aspect of the present invention is to provide a simplified on-line method to allow access to medication information.

DESCRIPTION OF THE PREFERRED EMBODIMENTS

The present invention discloses methods of generating and maintaining an on-line medication profile for use by a patient, their health care providers and anyone else to whom the patient gives access. The present methods are useful for providing complete medication information to a patient and/or their health care providers. Additionally, a patient may provide access to such information to anyone they choose, including, but not limited to, concerned relatives and adult children. Also, the method provides to a registered health care provider the medication information received by the patient, as well as additional medication information regarding medication side effects, drug-drug interactions, duplicative medical therapy, and drug contra-indications that will assist the health care provider in determining the proper medication regimen for the patient as well as identify and diagnose potential problems.

As used herein, the term "health care provider" means any health care personnel in need of medication information in order to make a medical decision regarding a patient. This term is intended to be defined as it is understood and used within the health care field. Examples of health care providers include, but are not limited to, physicians, nurses, and pharmacists.

As used herein, the term "medication profile provider" means the individual or entity receiving and/or generating the medical information as described herein and generating and providing access to a medication profile report.

As used herein, the term "user" means an individual or entity that is registered with the medication profile provider and has possession of a valid identification number and/or appropriate pass code from the medication profile provider in order to access and review medication information. By way of illustration, but not limitation, a user is a patient, a person possessing a patient's identification number and pass code, or a registered health care provider.

As used herein, the terms "medication specific data" or "patient medication information" (abbreviated as PMI) means information related to a specific medication in use by a patient and prescription information for any such medication. Examples include the name of the medication, the therapeutic class, drug monograph, name of the prescribing physician and contact information, instructions for taking the medication, prescription origination date, prescription exhaustion date, previous refill date of the prescription, expected next refill date of the prescription, the number of allowable refills, or patient compliance information (information regarding whether the patient is taking the medication as prescribed, as indicated by whether available refills have been timely obtained). The medication specific data may also include an index number assigned to the medication by the medication profile provider. When medication specific data is in the possession of the health care provider, normally a pharmacist, which dispensed a medication to a patient, such information may be known as "medication distribution information."

As used herein, the term "on-line data system" means an on-line data system as generally understood by one of skill in the art. An example of an on-line data system includes, but is not limited to, a web site that is accessible by entering login information.

As used herein, the term "harmful medication" means a medication with a therapeutic effect that merely duplicates the therapeutic effect of another medication that is prescribed to a patient, or a medication that interacts with a prescribed medication of a patient in a manner that is detrimental to the patient or a medication that should not be taken if a patient has a certain disease. The patient's possible diseases are identified based upon the authorized uses of the drugs being taken by the patient.

As used herein, the term "non-significant medical information" means medical information regarding a status or condition of a patient which is not severe or moderate. An example of non-significant medical information includes, but are not limited to, information regarding a side effect of a medication which is mild, such as dry throat.

As used herein, the term "non-significant profile information" means the same as non-significant medical information.

As used herein, the term "profile information" means information regarding the characteristics, prescriber information, directions for usage, and compliance information of the medication being used by the patient. Examples of profile information include the dispensing data, prescriber information, directions for usage, historical dispensing information, compliance data, therapeutic class, any to severe or moderate side effects which are probable, any severe or moderate drug-drug interaction which is probable, any severe or moderate disease contra indications which are probable, or other characteristics of each medication which may have a negative impact upon a patient which is greater than mild.

As used herein, the term "medication specific characteristics" means the medical characteristics of a medication. Databases of such known medical characteristics of any given medication are commercially available. An example of such a database is First DataBank, of San Bruno, Calif., as further described herein. The medical characteristics of a medication may be used to anticipate complications resulting from the use of that medication with another medication. Examples of medical characteristics of a medication include, but are not limited to, the therapeutic class, any side effects, any drug-drug interaction, any drug-disease contra indications, of each medication.

Any other terms not specifically defined herein are understood to have the usual meaning within the art.

Enrolling with a Medication Profile Provider

In order to use the on-line medication profile disclosed herein, it is necessary to take proper steps to be authorized to access such medical information. A patient may receive the necessary identification number and pass code by enrolling with the medication profile provider. Generally, enrollment requires that the patient provide his or her name, insurance and/or other payment information, as well as other demographic data so that he or she may receive an identification number and pass code. The exact steps of enrollment are not critical and may vary depending upon the medication profile provider. In alternate embodiments of the present invention, enrollment may additionally include the step of agreeing to have the medication profile provider dispense medications for the patient. Subsequent to enrollment, the patient may receive an identification card displaying his or her name, the identification number and the patient's pass code. Additionally, the back of the identification card may have instructions regarding how to use the identification number and pass code to access medical information.

A health care provider may also enroll with the medication profile provider in order to access the on-line medication profile of a patient. Registration of a health care provider results in an identification number and pass code being provided to the health care provider. The identification number may also be referred to as an identification code. As further described below, the health care provider may access the on-line medication profile of a patient by using the issued identification number and pass code and, in the case of a health care provider who registers with the medication profile provider, by entering the patient's social security number and date of birth. For registered health care providers, a higher level report is provided. If the person logged in to get the report is not identified by the medication profile provider as a registered health care provider, there is a limited set of information provided that does not include drug-drug interactions, drug disease interactions, side effects, and duplicate therapies. Other methods of accessing the profile information are disclosed herein.

Generating and Maintaining a Medication Profile

A medication profile provider must gather patient medication information to generate profile information. In certain embodiments of the present invention, the medication profile provider must gather Patient medication information as well as dispense medications to the patient in order to generate a complete medication profile. In certain embodiments of the present invention, the medication information of the patient may be obtained from a pharmaceutical distributor other than the medication profile provider, in order to ensure accurate information. In alternate embodiments of the present invention, the medical profile provider may be a pharmaceutical distributor for a patient and may access its own medication distribution information in order to obtain information regarding a patient. In still other embodiments of the present invention, the patient provides to the medication profile provider all medical information regarding medication usage and medication compliance as it relates to the medical history of the patient and the patient's current status.

Due to the probability of inaccurate information received directly from the patient, that manner of obtaining patient medication information is performed only when the data from a pharmaceutical distributor is not readily available. For example, when a new patient first enrolls with a medication profile provider that also is a pharmaceutical distributor, the medication profile provider may obtain data from the patient since other data may not be readily available. In certain embodiments of the present invention, patient medication information is obtained from the pharmaceutical distributor as part of the process of filling a prescription. However, after the initial enrollment of the patient, the medication profile provider which is also a pharmaceutical distributor, will rely upon medication distribution information as pharmaceutical distributions occur for that patient.

It is noteworthy that obtaining data from the pharmaceutical dispenser additionally provides the benefit of identifying patient noncompliance. For example, the records of a pharmacy will indicate that a patient was late in refilling a prescription. Such information is indicative of non-compliance by the patient. Similarly, data provided from the pharmaceutical dispenser includes the doctor's orders as to how the patient is to take each individual medication. Again, the accuracy of this information is highly reliable since the same data is printed on the instructions on the bottle. Furthermore, the information provided by the pharmaceutical distributor is accurate due to the need of the pharmacist to comply with pharmacy regulations related to patient information.

Examples of the type of medical information provided to the medication profile provider include, but are not limited to, the name of the medication, the name and contact information for the physician prescribing the medication, the date of the original prescription, information regarding the number of allowable refills, and instructions for taking the medication. Such detailed information is needed for each medication being used by the patient. Alternatively, a health care provider may provide the above-mentioned patient medication information on behalf of a patient under the care of the health care provider. The medical information provided by the patient or the health care provider is used to generate a medication profile as further described herein.

Figure 1:
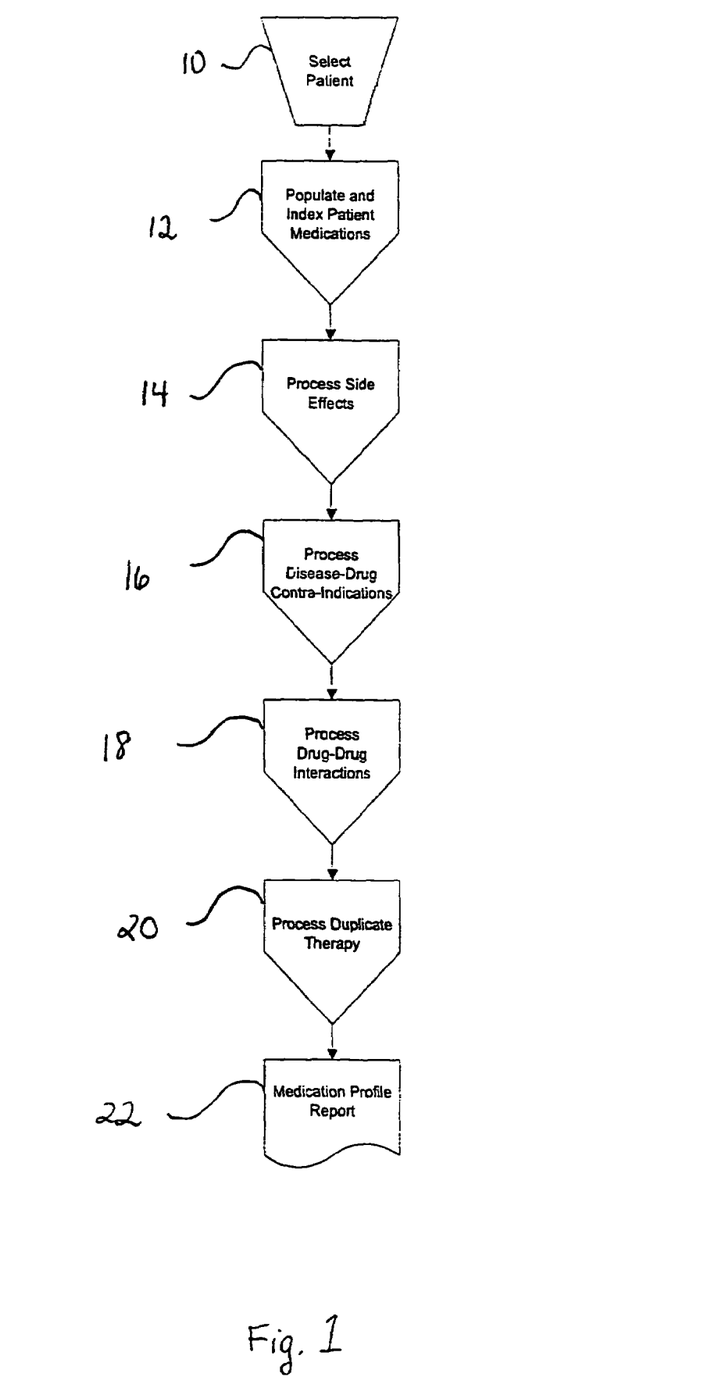
FIG. 1 is a block diagram of the steps for generating a medication profile report upon demand.

Once the patient medication information is entered by an individual, or the data is obtained from a pharmaceutical distributor or health care provider, the profile information is generated as further described herein. FIG. 1 shows a macro view of the steps taken to generate the report once a request for such a report has been made. Briefly, the patient is selected 10, the patient medications are populated and indexed 12, and further steps are taken to process, or identify, any side effects 14, disease-drug contra-indications 16, drug-drug interactions 18, and duplicative therapies 20 of each medication prescribed to the patient. After such profile information is generated, the non-significant medical information is not entered into the report and a medication profile report 22 is displayed. The above-mentioned steps of comparing the patient medication information to the medication specific characteristics available from an information database, may be performed by a computer system. More specifically, a software program has been written to perform the comparison. The software is currently written using File Maker Pro and PHP, which stands for PHP: Hypertext Preprocessor, with data extracted from Scriptmaster which is used to manage the dispensing of the prescription medications. The File Maker Pro software is commercially available from many sources including www.filemaker.com. The File Maker Pro software is also commercially available from FileMaker Inc. Corporate Headquarters, 5201 Patrick Henry Drive, Santa Clara, Calif. 95054-1171, or P.O. Box 58168, Santa Clara, Calif. 95052. The PHP software is available from many sources, including directly from the internet at www.php.net. Scriptmaster software is commercially available from many sources, including KeyCentrix, Inc., 245 N. Waco, Suite 100, Wichita, Kans. 67202, www.keycentrix.com. One of skill in the art may prepare computer code to accomplish the steps of the methods disclosed herein.

Referring to populating and indexing the patient's medications, as shown in FIG. 1, the computer system reviews the patient medication information provided by the dispensing data, the patient, or health care provider, to determine whether any medication was discontinued recently. If it is determined that a medication was recently discontinued then that medication name is added to the "Recently Discontinued Drugs" section of the medication profile. For medications which are currently being used by the patient, each medication is assigned an index number.

For each medication being used by the patient, the therapeutic class and uses of the medication are identified by comparing the patient medication information to a database containing medication specific characteristics. Such information regarding each medication is commercially available from a database that is well known in the art. In certain embodiments of the present invention, medication specific characteristics are provided by First DataBank (1111 Bay Hill Drive, San Bruno Calif. 94066, www.firstdatabank.com). In certain embodiments of the present invention, a software program is used to perform the comparisons and analysis described herein with regard to the patient medication information as it relates to the general medication data, also called medication specific characteristics, obtained from a database, such as First DataBank. In alternate embodiments of the present invention, other databases providing general medication data may be used.

The patient medication information provides detailed information about each medication used by the patient. For example, the patient medication information includes the name and contact information for the prescribing physician, instructions for use provided by the prescriber, original prescription date, last filled prescription date, next prescription refill date, the expiration date of the prescription, and, if the patient is past a due date for a prescription, the number of days the patient is past due for a refill. The order in which the above-mentioned information for each medication is entered into a computer system, or identified, is not critical to this invention. When it is stated that information is added to the medication profile report, it is understood that such information is entered into the data processing system.

Referring now to the identification of side effects 14, computer software is used to identify the medication being used by the patient from the patient medication information and is compared against the medication information database in order to identify all possible side effects and incorporate any such side effects into the medication profile. When a medication has a known side effect, the severity of that side effect is identified as well. Only side effects which have an impact upon the patient that is greater than mild will be provided in the profile information. Generally, severe and moderate side effects are included. Also, the primary system classification for each medication is identified by using the medication information database. The order of determining the severity and primary system classification of a side effect is not critical. Information regarding the side effects, severity of the side effects, and the primary system classification of each medication is within the profile information, or medication information, which is displayed to the user. In certain embodiments, a patient may be on more than one medication. In those situations, the above described steps are repeated for each medication being used by the patient with this information being aggregated in such manner as to only list each possible side effect one time on the medication profile with reference associated with each side effect indicating all of the patients medications that could be associated with each side effect.

In certain embodiments of the present invention, the side effects may be grouped by severity and primary system classification. Ultimately, all side effects of each medication used by the patient are represented within the profile information of the medication profile. In alternate embodiments of the present invention, the non-significant medical information, such as mild side effects, may be removed from the medication profile. In certain situations, the present invention may be used to identify significant medication problems for a patient that is on a complex medication plan, meaning they are on 5, 10, or more medications regularly. In such a situation, it is of primary significance that the serious, or severe, side effects be clearly identified and the less relevant side effect information is removed from the medication profile.

Referring now to the identification of disease drug contra indications 16, the medication profile provider identifies disease contra indications for each medication used by the patient. Disease contra indications are identified when the patient medication information is compared to the medication specific characteristics which are available from a known database. For example, in certain embodiments, a computer system compares the patient medication information to the information in the First DataBank to identify all possible diseases the patient may have based upon the patients medication regimen and compares these possible diseases that a patient may have to the FirstData Bank information detailing any diseases which should not be treated with the medication that the patient is using. Stated another way, certain medications and diseases should not be mixed. In certain cases, some medications may worsen disease symptoms. Thus, the patient's medication history may be compared to the disease contra indications of the medication profile to alert the potential problems of the distribution of certain medications to a patient. If a disease is indicated, then the potential severity of the reaction that could be received when a person having that disease takes a medication is identified. Information regarding the disease contra indications severity, and contra indicated medication index are entered into the medication profile. Only disease contra indications which have an impact upon the patient that is greater than mild will be provided in the profile information. Generally severe or moderate disease contra indications are included. In certain embodiments of the present invention, disease contra indications may be grouped by severity.

Referring now to the identification of drug-drug interactions 18, the medication profile provider also identifies information regarding drug-drug interactions. Drug-drug interactions are identified when the computer system compares each medication in use by the patient to the medication specific characteristics of each medication. It is noteworthy that only the drug-drug interactions concerning medications currently in use by the patient will be identified. The medication information database additionally provides information regarding the severity of any drug-drug interaction which is identified.

If a drug-drug interaction is identified, then the severity of the interaction is also identified. When a drug-drug interaction is identified, the name of the interacting drug and severity of the interaction are added to the medication profile. Only drug-drug interactions which have an impact upon the patient that is greater than mild will be provided in the profile information. Generally severe or moderate drug-drug interactions are included. In certain embodiments, the severity of the drug-drug interaction may be used to group the multiple drug-drug interactions. In alternate embodiment of the present invention, non-significant medical information, such as insignificant drug-drug interactions, may not be included on the medication profile since such insubstantial drug-drug interactions are not relevant to a patient on a complex medication regime which may produce significant, or even life threatening drug-drug interactions.

Referring now to the identification of duplicate therapy 20, steps are taken to identify prescribed medications in use by the patient that are providing medication therapy which is duplicative of another medication in use by the patient. The therapeutic class of each medication is identified by the computer system by comparing each medication within the patient medication information against the information in the databank. The identified therapeutic classes of each medication to are a part of the profile information and are included in the medication profile. In certain embodiments, information regarding the duplication of therapeutic activities of medications may be used to modify the medication schedule of the patient. For example, if two medications are within the same therapeutic class, then a health care provider may determine that one of the medications is duplicative in effect and instruct the patient to stop using such medication. In still other embodiments of the present invention, the absence of the duplication of therapeutic classes is an indication that the medication profile of the patient is proper.

Figure 2:
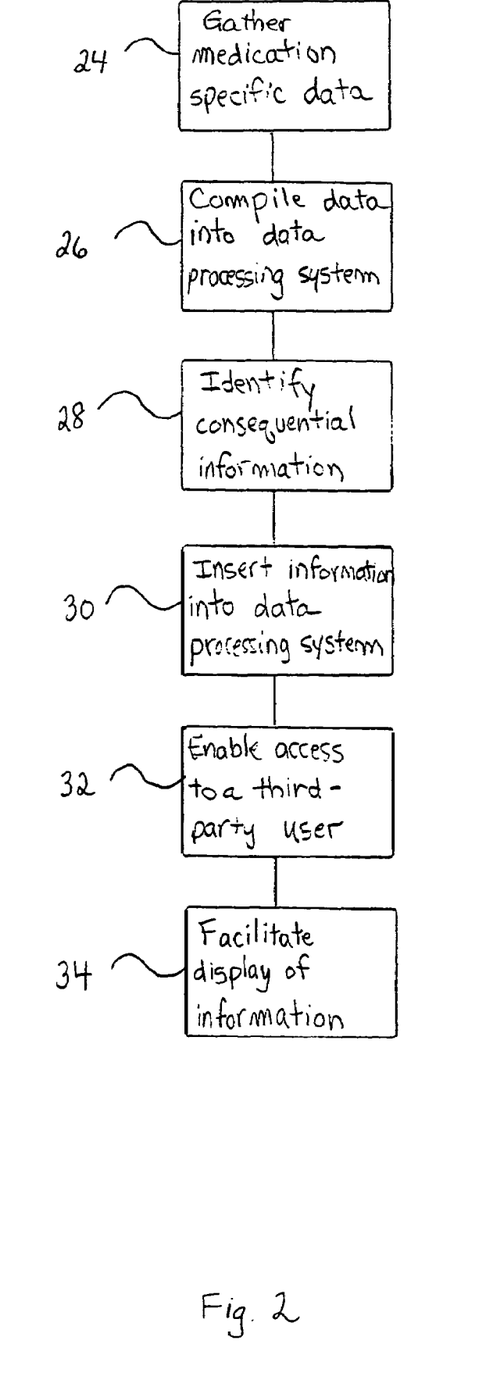
FIG. 2 is a block diagram showing the steps for performing a medical information processing method, as further described herein.

As shown in FIG. 2, the present invention includes a medical information processing method, including the steps of (a) gathering medication-specific data 24 for the medication of a patient from a plurality of independent sources, (b) compiling the data into a data processing system 26, (c) identifying consequential information 28, by identifying at least one item of consequential information from the following group: a side effect of the medication, a drug-drug interaction of the medication, and a therapeutic class of the medication, (d) inserting the consequential information into a data processing system 30, by inserting the at least one item into the data processing system, (e) enabling a third-party user to access 32 the information and item from a location remote from the location of the data processing system, and (f) facilitating a display of the item 34 to the user. In certain embodiments, the present invention also includes the above-method wherein facilitating the display of the item to the user includes the step of facilitating the display of the side effect of the medication which is severe and probable, and the therapeutic class of the medication to the user. In other certain embodiments of the invention, identifying at least one item of consequential information may also include identifying a disease contra indication of the medication and the step of facilitating the display of the item to the use includes facilitating the display of the disease contraindication of the medication to the user.

In still other embodiments of the present invention, the step of enabling a third-party user to access the information 32 and item from a location remote from the location of the data processing system of the above-described method, further includes assigning the user an identification code, assigning the user a pass code, and upon entry of an identification code and pass code, comparing the entered identification code and the pass code to the assigned identification code and the assigned pass code to authorize access to the information and item.

Additionally, the present invention includes a medical information processing method wherein gathering medication-specific data 24 for the medication of a patient from a plurality of independent sources the medication-specific data includes at least one of the items of data selected from the following group; the name of the medication, and administration dose of the medication, the name of a health care provider that prescribed the medication, the original date of the prescription for the medication, the date of exhaustion of the prescription for the medication, a set of instructions for administering the medication, and compliance information for the medication. In certain embodiments, the present invention also includes a medication information processing method wherein the step of gathering medication-specific data 24 for the medication of a patient from a plurality of independent sources, the medication-specific data includes information indicative of patient usage of prescribed medications and with regard to step (c) the consequential information includes information regarding the indicated patient usage of prescribed medications. In other embodiments, enabling access to a third-party user 32, step (e) above, includes enabling a health care provider to submit a proposed new medication and obtain additional consequential information relating to the addition of the new medication to patient's medication. In still other embodiments of the present invention, step (e) includes enabling a selected class of users to access less than all of the consequential information.

The present invention additionally includes a method profiling the medication history of a patient, including collecting the patient medication information from medication distribution information of a plurality of health care providers, integrating the information into a data system that is accessible on-line, comparing the patient medication information to a drug-drug interaction database in order to identify severe and moderate drug-drug interactions, comparing the patient medication information to a disease contraindication database in order to identify severe and moderate disease contraindications, compiling in the data system the identified drug-drug interaction and category of severity of the drug-drug interaction and the identified disease contraindication and category of severity of disease contraindication, and facilitating access to information in the data system by a user through an on-line connection. In certain embodiments of the present invention, this method further includes the step of facilitating the display of the patient medication information to a user accessing the data system by providing a patient identification number and a patient pass code. In still other embodiments, with regard to this method of profiling the medication history of a patient, the patient medication information further includes at least one item of information taken from the following group: the name of the medication, an administration dose of the medication, a name of a health care provider that prescribed the medication, an original date of a prescription of the medication, the date of exhaustion of the prescription for the medication, a set of instructions for administering the medication, and compliance information for the medication.

In still other embodiments, the method of profiling the medication history of the patient further includes the step of facilitating display of severe and moderate drug-drug interactions and severe and moderate disease contraindications to a user entering a health care provider identification number and pass code. In other embodiments, the method also includes the step of determining indicated patient usage of the medications.

In still other embodiments of the present invention, the method of profiling the medication history of a patient includes the step of enabling a health care provider to submit a proposed new medication, and comparing the proposed new medication to both the databases to identify further drug-drug interactions and disease contraindications. In another embodiment of the method of profiling the medication history of a patient includes the limitation that a select class of users is facilitated access to less than all of the information.

Figure 3:
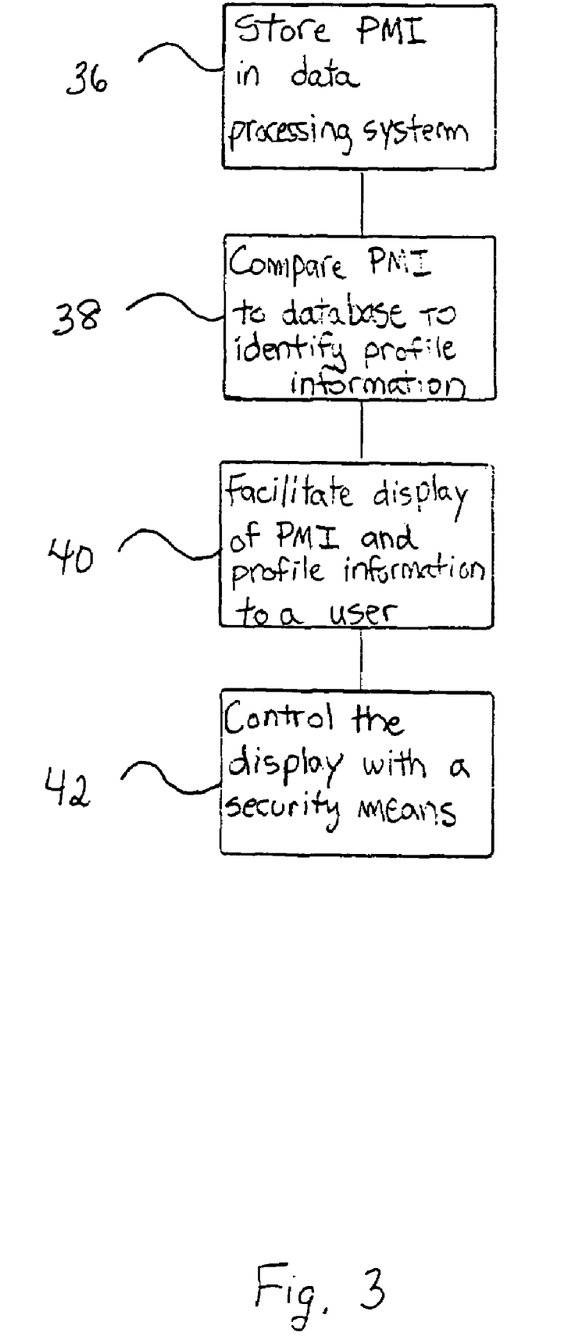
FIG. 3 is a block diagram showing the steps for a method of generating a medical profile for a patient.

Referring now to FIG. 3, there is shown a block diagram of a method of generating a medical profile for a patient including the steps of (a) storing in a data processing system, patient medication information 36 including medication distribution information obtained from a health care provider, (b) comparing the patient medication information to a database to identify profile information 38, (c) facilitating the display of the patient medication information and profile information 40 to a user, and (d) controlling the display 42 of the patient medication information and profile information by providing an identification code and pass code to the user that must be entered for the use to gain access to the information. In certain embodiments of this method, step (a) further includes entering into the data processing system patient medication information including medication distribution information obtained from a plurality of health care providers. In another embodiment of this method, within step (b), the profile information includes a severe side effect of the medication, a severe drug-drug interaction of the medication, and a therapeutic class of the medication.

The present invention additionally includes a method of providing medication information, including steps of (a) entering into a data processing system patient medication information originating from a health care provider previously distributing medication to a patient, and (b) facilitating the display of the patient medication information to a user other than the patient wherein the patient possesses information to access the data processing system in order to display the patient medication information and the patient provides the information to access the data processing information system to the user so that the user accesses the data processing system in order to display the patient medication information. In certain embodiments of this method, step (a) further includes entering into the data processing system patient medication information from a plurality of heath care providers previously prescribing medication to the patient.

In other embodiments of this method, the method further includes accessing a database containing medication specific characteristic, comparing the patient medication information and the medication-specific characteristics, generating profile information, and displaying the profiling information to the user. In certain embodiments of the method listed in the previous sentence, the profile information includes a severe side effect of the medication, a severe drug-drug interaction of the medication, and a therapeutic class of the medication.

In still other embodiments of the method of providing medication to information, within step (a), patient medication information further includes: the name of a medication in use by the patient, an administration dose of the medication, the name of a health care provider that prescribed the medication, the origination date of the prescription for the medication, the date of the exhaustion of the prescription for the medication, a set of instructions for administering the medication, and compliance information for the medication.

Figure 4:
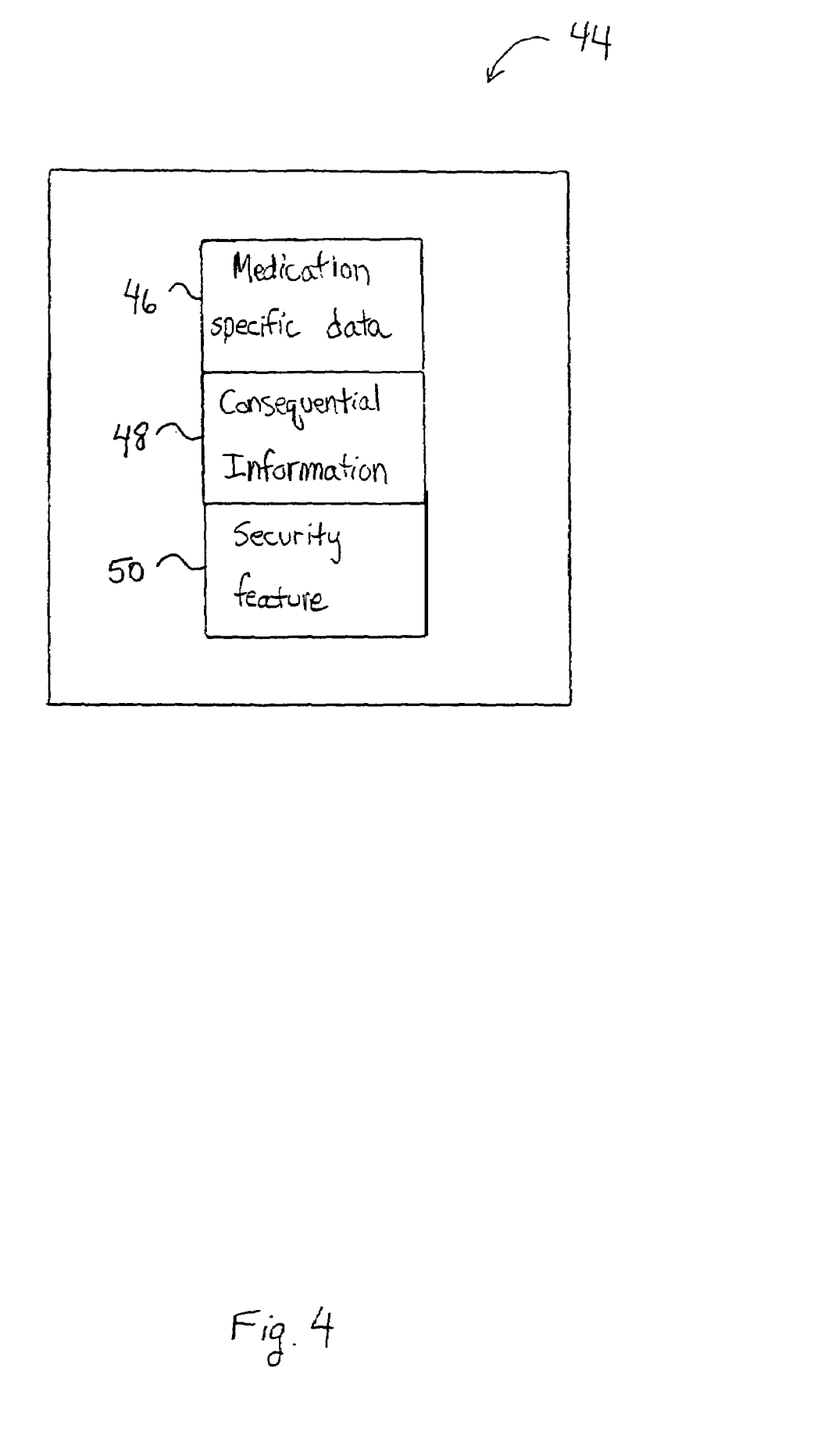
FIG. 4 is a schematic diagram showing the medical information database. The database contains medication specific data for the medications prescribed to a patient and consequential information about the prescribed medications. The database provides secured access to the information it contains.

Referring now to FIG. 4, there is shown a schematic diagram of the medical information database 44. The medical information database 44 includes a patient profile database including for each patient a patient profile. The patient profile includes medication specific data 46 for the medications which have been prescribed to the patient, and consequential information 48, including identification of any drug-drug interactions of the prescribed medications. The medical information database 44 also includes a security feature 50. The security feature 50 provides secured access to the patient profiled database requiring entry of and identification number and pass code in order for a user to gain access to a patient's profile. In certain embodiments of this database, the consequential information further includes side effects of the medications. In still other embodiments of the database, the consequential information further includes identification of multiple medications in a therapeutic class as a possible indication of duplicative medication. In still other embodiments of the database, the consequential information further includes identification of disease drug contraindications. In certain embodiments of the database, the medication specific data includes information indicative of actual patient usage of the prescribed medications, and the consequential information includes information regarding the indicated actual patient usage of prescribed medications. In still other embodiments of the database, the secured access permits the selected class of users to access less than all of the consequential information in the patient profile.

Using the Online Medication Profile

Medical information may be obtained from the medication profile by registered users through an on-line format. A registered patient having an identification number and a pass code or a registered health care provider having an identification number and pass code, may access a website provided by the medication profile provider. In certain embodiments of the present invention, a registered patient may be given an identification card, which includes the identification number, pass code, and instructions for obtaining the medication report as further disclosed herein. Accordingly, the possessor of the identification card has sufficient information in order to obtain the medication report. In certain embodiments of the present invention, the medication profile provider has a website such as www.maxwellmedical.com.

A registered health care provider may gain access to medication information by entering an identification number and pass code. After verification of the identification number and pass code, the provider's accession of medication information is approved and the provider can obtain medication information for a specific patient either by entering a patient's social security number and date of birth, or by entering the patient's identification number and pass code. The data processing system of the medication profile provider identifies medical information regarding the requested patient and the system logs the provider's access to the patient records. A log is also entered on the record of the patient. After the medication profile report is generated, it is displayed on-line and the report is also available in printed form.

An individual patient may also obtain his or her medication information by entering an identification number and pass code which is verified and approved by the medication profile provider. The data processing system of the medication profile provider logs the access into the record. A medication profile report is displayed on-screen. The on-screen medication profile report may also be available in printed form.

As stated above, the medication profile report includes, but is not limited to, the following information regarding each drug, or medication: name of the drug, concentration of the drug, "treatment class" of the drug, name and contact information of the provider that prescribed the drug, the original date of the prescription of the drug, the date on which the patient is expected to exhaust all refill supplies of the drug, the date the drug was last provided to the patient, the supply remaining to be dispensed to the patient upon their request, the number of days a patient is past due if a refill has not occurred, the expected date of the next refill of the prescription, medication instructions for the drug, and uses of the drug. The above-mentioned information is available to the patient and the health care provider.

In certain embodiments of the present invention, a difference in the type and amount of medication information in the medication profile report exists and is dependent upon the user's status. In certain embodiments, a registered health care provider will be provided the following profile information within the medication profile report: the names of any medications that the patient has discontinued use of within the previous two months, the names of medications that may be interfering with the therapeutic characteristics of another drug, possible drug-drug interactions, possible side effects a patient may experience and the name of the medication causing the side effect.

In certain embodiments, a health care provider may add the name of a medication to the patient medication information in order to check the medication for any conflicts or problems with the other medications being used by the patient. When this option is used, obviously there is no prescription information available in the medication profile report since the new medication has not been prescribed or distributed to the patient. In certain embodiments of the present invention, the website provided by the medication profile provider has security measures to ensure that the patient's medication information is not accessed by people other than those that have proper authority to obtain such medication information.

Figure 5:
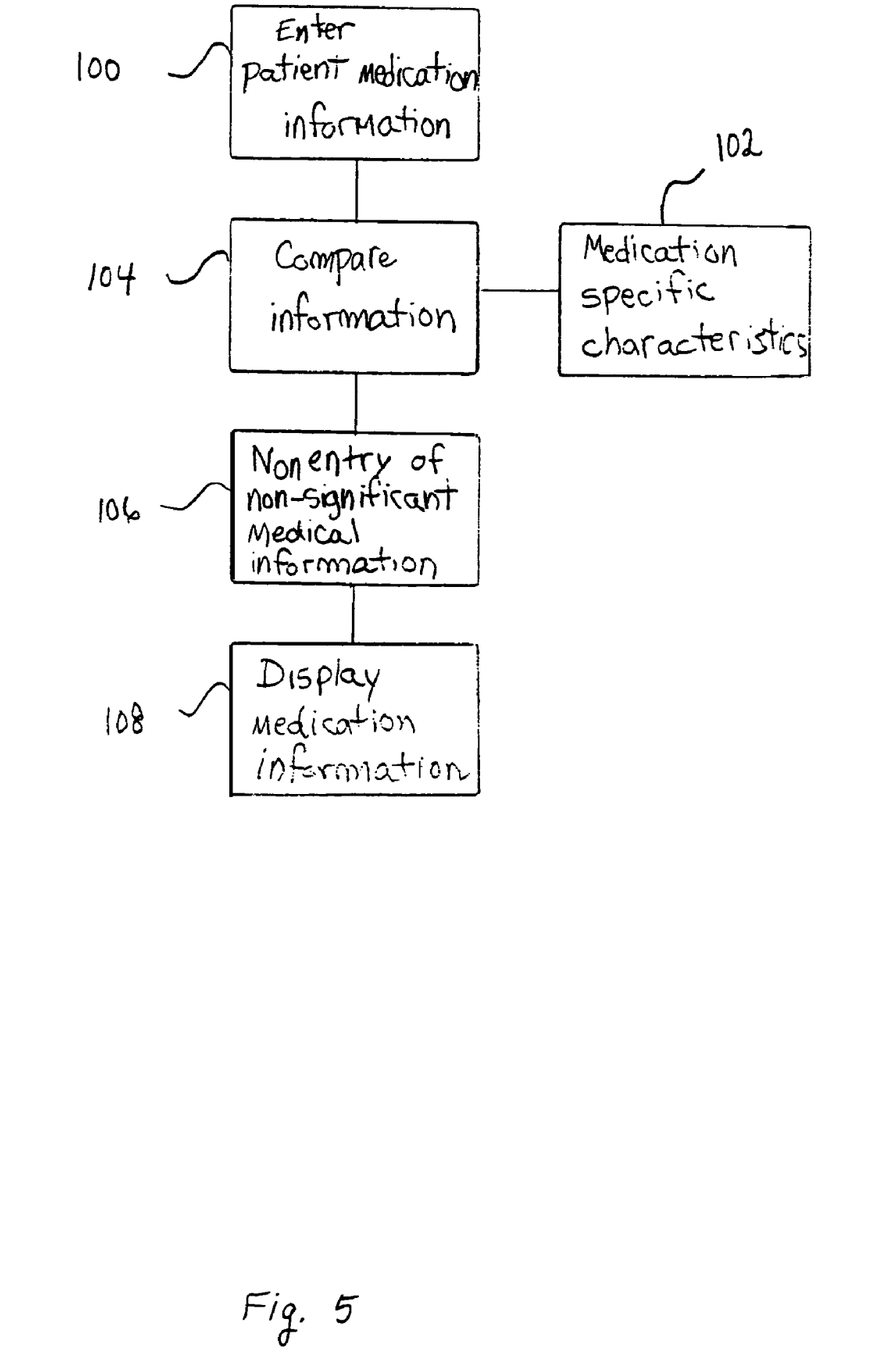
FIG. 5 is a block diagram of a method of reporting medical information.

Thus, as shown in FIG. 5, patient medication information 100 and medication specific characteristics 102 are compared 104 in order to generate the profile information. As described herein, any non-significant information 106 is not entered and the profile information is displayed 108 to the user.

Although the medical information processing system of the present invention has been described herein primarily in its preferred on-line assessable environment, the system can also be accessed other than via the Internet. For example, the system could be accessed remotely via a hardwired system. In some aspects the system could be accessed on site, rather than remotely. The patient profile database could also be provided in a downloaded database, or via hard copy such as a CD, and the database could be periodically updated.

This patent application incorporates by reference all references and publications disclosed herein. Thus, it is seen that the methods and database of the present invention readily achieve the ends and advantages mentioned as well as those inherent therein. While certain preferred embodiments of the invention have been illustrated and described for purposes of the present disclosure, numerous changes in the arrangement of the steps may be made by those skilled in the art, which changes are encompassed within the scope and spirit of the present invention as defined by the to following claims.

EXAMPLES

1. Content of a Medication Profile Report

The following is an example of a medication profile report that may be generated by a medication profile provider for a user logging on with a patient identification number and pass code. Note that the medication profile provided to such a user merely includes a summary of the medication and does not include information regarding recently discontinued drugs, possible duplicate therapy, possible drug-drug interactions and possible side effects.

---

Medication Profile for . . .  
Mr. Example Patient 123-45-6789

Pharmacist: Catherine Burkhart, Pharm. D.  
Toll Free: (800) 292-9143  
maxwellmedical.com 1 - ASPIRIN 81 MG TABLET EC — ANALGESIC/ANTIPYRETICS, SALICYLATES
- Prescriber: Dr. George H Crossley (615) 329-5144
- Original Rx Date: Oct. 31, 2002 — Orders Expected to Run Out: 60 days after next fill
- Last Filled: Unknown — Refill Due (Based on Last Fill): Not Applicable
- Directions: Take 1 Tablet By Mouth Every Day
- Not Supplied by MAX Well Medical.
- USES: Aspirin is used to relieve mild to moderate pain, reduce fever, to reduce inflammation and swelling in conditions such as arthritis and is used in low doses as a "blood thinner" to prevent the formation of blood clots. It is effective in reducing the risk of stroke and offers a protective effect against heart attacks in men with chest pain.

2 - CAPTOPRIL 50 MG TABLET — HYPOTENSIVES, ACE INHIBITORS
- Prescriber: Ms. Dorothy A Cloyd (615) 414-1347
- Original Rx Date: Dec. 19, 2002 — Orders Expected to Run Out: 150 days after next fill
- Last Filled: Jan. 17, 2003 — Refill Due (Based on Last Fill): Feb. 16, 2003(173 days overdue
- Directions: Take 1 Tablet By Mouth Two Times Daily For Blood Pressure
- USES: Captopril belongs to a group of drugs called "ACE inhibitors." ACE inhibitors prevent certain enzymes in the body from constricting blood vessels. This helps to lower blood pressure and makes the heart beat stronger. This medication is used to treat hypertension (high blood pressure), heart failure and kidney disease in certain diabetic patients.

3 - GEMFIBROZIL 600 MG TABLET — LIPOTROPICS
- Prescriber: Ms. Dorothy A Cloyd (615) 414-1347
- Original Rx Date: Dec. 19, 2002 — Orders Expected to Run Out: Mar. 10, 2004 (215 days)
- Last Filled: Jul. 14, 2003 — Refill Due (Based on Last Fill): Aug. 13, 2003
- Directions: Take 1 Tablet By Mouth Two Times Daily 30 Minutes Before Meals For Cholesterol
- USES: This medication is used to lower high cholesterol and/or triglyceride levels in the blood. High levels of cholesterol or triglycerides may block the blood vessels, increasing the risk of heart disease. For best results, this medication must be used along with an exercise program and a low-cholesterol, low-fat diet.

4- METOPROLOL 50 MG TABLET — BETA-ADRENERGIC BLOCKING AGENTS
- Prescriber: Ms. Dorothy A Cloyd (615) 414-1347
- Original Rx Date: Feb. 13, 2003 — Orders Expected to Run Out: Oct. 12, 2003 (65 days)
- Last Filled: Jul. 14, 2003 — Refill Due (Based on Last Fill): Aug. 13, 2003
- Directions: Take ½ Tablet By Mouth Two Times Daily
- USES: This medication is used for chest pain (angina), high blood pressure and irregular heartbeats.

5 - NITROGLYCERIN 2.5 MG CAP SA — VASODILATORS,CORONARY
- Prescriber: Dr. George H Crossley (615) 329-5144
- Original Rx Date: Dec. 16, 2002 — Orders Expected to Run Out: Dec. 11, 2003 (125 days)
- Last Filled: Jul. 14, 2003 — Refill Due (Based on Last Fill): Aug. 13, 2003
- Directions: Take 1 Capsule By Mouth Two Times Daily
- USES: This medication relaxes blood vessels allowing more blood to flow through. This improves blood flow to the heart. Oral dose forms are used to prevent angina (chest pain). This medication is NOT for treating an attack of chest pain that is already happening.

6- NITROSTAT 0.4 MG TABLET SL — VASODILATORS,CORONARY
- Prescriber: Dr. George H Crossley (615) 329-5144
- Original Rx Date: Oct. 31, 2002 — Orders Expected to Run Out: 500 days after next fill
- Last Fliled: Unknown — Refill Due (Based on Last Fill): Not Applicable
- Directions: Take As Directed
- USES: Nitroglycerin relaxes blood vessels allowing more blood to flow through. This reduces the workload on the heart and improves blood flow to the heart. Sublingual nitroglycerin tablets act quickly to relieve chest pain (angina).

7 - PHENAZOPYRIDINE 200 MG TAB — URINARY TRACT ANESTHETIC/ANALGESIC AGNT (AZO-DYE)
- Prescriber: Dr. Melvin Lightford (615) 254-9981
- Original Rx Date: Feb. 17, 2003 — Orders Expected to Run Out: Feb. 19, 2003
- Last Filled: Feb. 17, 2003 — Refill Due (Based on Last Fill): No Authorized Refills
- Directions: Take 1 Tablet By Mouth Three Times Daily For 2 Days
- USES: This medication is used to relieve pain, burning and discomfort of the urinary tract.

8- POTASSIUM CL 10 MEQ CAP SA — POTASSIUM REPLACEMENT
- Prescriber: Ms. Dorothy A Cloyd (615) 414-1347
- Original Rx Date: Feb. 14, 2003 — Orders Expected to Run Out: Oct. 12, 2003 (65 days)
- Last Filled: Jul. 14, 2003 — Refill Due (Based on Last Fill): Aug. 13, 2003
- Directions: Take 1 Capsule By Mouth Two Times Daily
- USES: This medication is used to prevent or treat low potassium blood levels caused by "water pills" (diuretics) or poor diet.

9 - PROPAFENONE HCL 150 MG TAB — ANTIARRHYTHMICS
- Prescriber: Dr. George H Crossley (615) 329-5144
- Original Rx Date: Dec. 16, 2002 — Orders Expected to Run Out: Dec. 11, 2003 (125 days)
- Last Filled: Jul. 14, 2003 — Refill Due (Based on Last Fill): Aug. 13, 2003

-continued

| | | |
|---|---|---|
| Directions: | Take 1 Tablet By Mouth Three Times Daily | USES: This medication is used to treat irregular heartbeats (arrhythmias) and maintain a normal heart rate. |
| 10 - TRIAMTERENE/HCTZ 37.5/25 CP | | POTASSIUM SPARING DIURETICS IN COMBINATION |
| Prescriber: | Dr. George H Crossley | Original Rx Date: Dec. 16, 2002   Orders Expected to Run Out: Dec. 11, 2003 (125 days) |
| | (615) 329-5144 | Last Filled: Jul. 14, 2003   Refill Due (Based on Last Fill): Aug. 13, 2003 |
| Directions: | Take 1 Capsule By Mouth Every Day | USES: This drug is a diuretic or "water pill". It reduces the amount of water and sodium retained by the body. It is used to lower blood pressure and to treat edema (fluid retention). |

2. Content of a Medication Profile Report
Distributed to A Registered Provider

The following is an example of a medication profile report that may be provided to a registered health care provider. Note that detailed profile information is included on this report. Such information is not available to a user logging on with the patient's identification number and pass code.

---

Medication Profile for . . .   Pharmacist: Catherine Burkhart, Pharm. D.
Mr. Example Patient 123-45-6789   Toll Free: (800) 292-9143
  maxwellmedical.com 1 - ASPIRIN 81 MG TABLET EC   ANALGESIC/ANTIPYRETICS, SALICYLATES
Prescriber:   Dr. George H Crossley   Original Rx Date: Oct. 31, 2002   Orders Expected to Run Out: 60 days after next fill
  (615) 329-5144   Last Filled: Unknown   Refill Due (Based on Last Fill): Not Applicable
Directions:   Take 1 Tablet By Mouth Every Day   USES: Aspirin is used to relieve mild to moderate pain, reduce fever, to reduce
Not Supplied by MAX Well Medical.   inflammation and swelling in conditions such as arthritis and is used in low doses as a
  "blood thinner" to prevent the formation of blood clots. It is effective in reducing the riot
  of stroke and offers a protective effect against heart attacks in men with chest pain.

2 - CAPTOPRIL 50 MG TABLET   HYPOTENSIVES, ACE INHIBITORS
Prescriber:   Ms. Dorothy A Cloyd   Original Rx Date: Dec. 19, 2002   Orders Expected to Run Out: 150 days after next fill
  (615) 414-1347   Last Filled: Jan. 17, 2003   Refill Due (Based on Last Fill): Feb. 16, 2003(173 days overdue)
Directions:   Take 1 Tablet By Mouth Two Times   USES: Captopril belongs to a group of drugs called "ACE inhibitors." ACE inhibitors prevent
  Daily For Blood Pressure   certain enzymes in the body from constricting blood vessels. This helps to lower blood
  pressure and makes the heart beat stronger. This medication is used to treat hypertension (high
  blood pressure), heart failure and kidney disease in certain diabetic patients.

3 - GEMFIBROZIL 600 MG TABLET   LIPOTROPICS
Prescriber:   Ms. Dorothy A Cloyd   Original Rx Date: Dec. 19, 2002   Orders Expected to Run Out: Mar. 10, 2004 (215 days)
  (615) 414-1347   Last Filled: Jul. 14, 2003   Refill Due (Based on Last Fill): Aug. 13, 2003
Directions:   Take 1 Tablet By Mouth Two Times   USES: This medication is used to lower high cholesterol and/or triglyceride levels in the
  Daily 30 Minutes Before Meals For   blood. High levels of cholesterol or triglycerides may block the blood vessels, increasing
  Cholesterol   the risk of heart disease. For best results, this medication must be used along with an
  exercise program and a low-cholesterol, low-fat diet.

4 - METOPROLOL 50 MG TABLET   BETA-ADRENERGIC BLOCKING AGENTS
Prescriber:   Ms. Dorothy A Cloyd   Original Rx Date: Feb. 13, 2003   Orders Expected to Run Out: Oct. 12, 2003 (65 days)
  (615) 414-1347   Last Filled: Jul. 14, 2003   Refill Due (Based on Last Fill): Aug. 13, 2003
Directions:   Take ½ Tablet By Mouth Two Times Daily   USES: This medication is used for chest pain (angina), high blood pressure and irregular heartbeats.

5 - NITROGLYCERIN 2.5 MG CAP SA   VASODILATORS,CORONARY
Prescriber:   Dr. George H Crossley   Original Rx Date: Dec. 16, 2002   Orders Expected to Run Out: Dec. 11, 2003 (125 days)
  (615) 329-5144   Last Filled: Jul. 14, 2003   Refill Due (Based on Last Fill): Aug. 13, 2003
Directions:   Take 1 Capsule By Mouth Two Times   USES: This medication relaxes blood vessels allowing more blood to flow through. This
  Daily   improves blood flow to the heart. Oral dose forms are used to prevent angina (chest pain).
  This medication is NOT for treating an attack of chest pain that is already happening.

6 - NITROSTAT 0.4 MG TABLET SL   VASODILATORS,CORONARY
Prescriber:   Dr. George H Crossley   Original Rx Date: Oct. 31, 2002   Orders Expected to Run Out: 500 days after next fill
  (615) 329-5144   Last Filled: Unknown   Refill Due (Based on Last Fill): Not Applicable
Directions:   Take As Directed   USES: Nitroglycerin relaxes blood vessels allowing more blood to flow through. This
  reduces the workload on the heart and improves blood flow to the heart. Sublingual
  nitroglycerin tablets act quickly to relieve chest pain (angina).

7 - PHENAZOPYRIDINE 200 MG TAB   URINARY TRACT ANESTHETIC/ANALGESIC AGNT (AZO-DYE)
Prescriber:   Dr. Melvin Lightford   Original Rx Date: Feb. 17, 2003   Orders Expected to Run Out: Feb. 19, 2003
  (615) 254-9981   Last Filled: Feb. 17, 2003   Refill Due (Based on Last Fill): No Authorized Refills
Directions:   Take 1 Tablet By Mouth Three Times   USES: This medication is used to relieve pain, burning and discomfort of the urinary tract.
  Daily For 2 Days 8 - POTASSIUM CL 10 MEQ CAP SA   POTASSIUM REPLACEMENT
Prescriber:   Ms. Dorothy A Cloyd   Original Rx Date: Feb. 14, 2003   Orders Expected to Run Out: Oct. 12, 2003 (65 days)
  (615) 414-1347   Last Filled: Jul. 14, 2003   Refill Due (Based on Last Fill): Aug. 13, 2003
Directions:   Take 1 Capsule By Mouth Two Times   USES: This medication is used to prevent or treat low potassium blood levels caused by
  Daily   "water pills" (diuretics) or poor diet.

9 - PROPAFENONE HCL 150 MG TAB   ANTIARRHYTHMICS
Prescriber:   Dr. George H Crossley   Original Rx Date: Dec. 16, 2002   Orders Expected to Run Out: Dec. 11, 2003 (125 days)

-continued

|  | (615) 329-5144 | Last Filled: Jul. 14, 2003 | Refill Due (Based on Last Fill): Aug. 13, 2003 |
|---|---|---|---|
| Directions: | Take 1 Tablet By Mouth Three Times Daily | USES: This medication is used to treat irregular heartbeats (arrhythmias) and maintain a normal heart rate. | |
| 10 - TRIAMTERENE/HCTZ 37.5/25 CP | | | POTASSIUM SPARING DIURETICS IN COMBINATION |
| Prescriber: | Dr. George H Crossley | Original Rx Date: Dec. 16, 2002 | Orders Expected to Run Out: Dec. 11, 2003 (125 days) |
|  | (615) 329-5144 | Last Filled: Jul. 14, 2003 | Refill Due (Based on Last Fill): Aug. 13, 2003 |
| Directions: | Take 1 Capsule By Mouth Every Day | USES: This drug is a diuretic or "water pill". It reduces the amount of water and sodium retained by the body. It is used to lower blood pressure and to treat edema (fluid retention). | |

Recently Discontinued Drugs: Drugs that have been discontinued within the last 2 months
None (according to our records)
Possible Duplicate Therapy: Drugs that belong to the same therapeutic class
VASODILATORS,CORONARY: (5), (6)
Possible Drug—Drug Interactions: Drug—Drug Interactions are categorized as 'Absolute', 'Severe', or 'Moderate'.
Numbers in parentheses indicate drugs listed above which participate in the possible drug—drug interaction shown.

| ABSOLUTE: | None. |
|---|---|
| SEVERE: | POTASSIUM PREPS/POTASSIUM SPARING DIURETICS: (8) may interact with (10) |
| MODERATE: | ACE INHIBITORS/POTASSIUM SPARING DIURETICS: (2) may interact with (10) |
|  | ACE INHIBITORS/POTASSIUM PREPARATIONS: (2) may interact with (8) |
|  | BETA-BLOCKERS/PROPAFENONE: (4) may interact with (9) |

Possible Side Effects: Side Effects are categorized as 'Severe' or 'Moderate' and listed alphabetically. Numbers in parentheses indicate drugs listed above which, according to the manufacturer, may contribute to the side effect shown.

| SEVERE: | CARDIOVASCULAR DISORDER: Angina Pectoris(9) Atrial Fibrillation(9) Atrial Flutter(9) Atrioventricular Block(9) Bradycardia(9) Bundle Branch Block(9) Cardiac Arrhythmias(4) Cardiac Conduction Abnormalities(9) Congestive Heart Failure(4, 9) Hypotension(2, 9) Orthostatic Hypotension(4) Ventricular Tachycardia(9) |
|---|---|
|  | DERMATOLOGIC DISORDERS: Allergic Angioedema(1, 2) Allergic Dermatitis(1, 5, 6, 7, 10) Erythema(1) Skin Rash(1, 2, 5, 6, 7, 10) Urticana(1, 10) |
|  | EENT-DENTAL: Blurred Vision(5, 6) Sore Throat(8) Xerostomia(5, 6) |
|  | GASTROINTESTINAL DISORDER: Bloody Stools(8) Cholecystitis(10) Gallbladder Disease(3) Gallstone Disease(3) Gastrointestinal Hemorrhage(1) Gastrointestinal Irritation(8) Gastrointestinal Ulcer(1) Hepatic Disease(10) Hyperuricemia(10) Toxin-related Hepatitis(2, 7) |
|  | GENITOURINARY/NEONATOLOGIC DISEASE: Acute Renal Disease(2) Renal Calculi(10) Renal Disease(2, 7) Renal Failure(7) |
|  | HEMATOLOGIC DISORDERS: Agranulocytosis(2, 9, 10) Anemia(1, 3) Hemolytic Anemia(1, 7) Leukopenia(3, 4) Methemoglobinemia(7) Neutropenia(2) Thrombocytopenia(4, 10) |
|  | INFECTIOUS DISEASE: Aseptic Meningitis(7) |
|  | NERVOUS SYSTEM/PSYCHIATRIC DISORDERS: Acute Confusional State(4) Depression(4) Hallucinations(4) Severe Headache(5, 6) Tremors(9) |
|  | NUTRITIONAL/METABOLIC DISORDER: Electrolyte Imbalance(10) Fever(2) Gout(10) Hyperkalemia(2, 8, 10) Hypochloremia(10) Hypokalemia(10) Hyponatremia(10) |
|  | ORTHOPEDICS: Arthralgia(2, 4, 9) Back Pain(4) Myositis(3) |
|  | PULMONARY DISORDER: Bronchospastic Pulmonary Disease(1, 4) Dyspnea(1, 10) Wheezing(1) |
|  | UNCLASSIFIED: Acute Pancreatitis(2, 10) Allergic Reactions(1, 4, 5, 6, 7, 10) Anaphylaxis(1, 10) Chest Pain(2, 4) Dizziness(4) Jaundice(7, 10) Laryngeal Edema(2) Peripheral Vasoconstriction(4) Proteinuria(2) Pruritus(1, 10) Psoriasiform Eruption(4) Supraventricular Paroxysmal Tachycardia(9) |
| MODERATE: | CARDIOVASCULAR DISORDER: Orthostatic Hypotension(5, 6, 10) Tachycardia(5, 6) |
|  | DERMATOLOGIC DISORDERS: Flushing(5, 6) Skin Photosensitivity(10) Skin Rash(3, 9) |
|  | EENT-DENTAL: Blurred Vision(9) Dry Eyes(4) Dysgeusia(2, 4, 9) Ocular Imitiation(4) Xerostomia(9) |
|  | GASTROINTESTINAL DISORDER: Abdominal Pain with Cramps(1, 3, 4, 7, 8, 10) Anorexia(10) Constipation(4,9) Diarrhea(2, 3, 4, 8, 9, 10) Flatulence(3, 8) Gastrointestinal imitation(1, 10) Heartburn(1, 3) Hypersecretory Conditions(1) Nausea(1, 2, 3, 4, 5, 6, 8, 9) Vomiting(1, 3, 4, 5, 6, 8, 9) |
|  | GENITOURINARY/NEONATOLOGIC DISEASE: Sexual Function Impairment(4, 10) |
|  | NERVOUS SYSTEM/PSYCHIATRIC DISORDERS: Anxiety(4) Fatigue(2, 3, 4, 9) Insomnia(4) Nervousness(4, 5, 6) Nightmares(4) |
|  | PULMONARY DISORDER: Cough(2) Nasal Congestion(4) |
|  | UNCLASSIFIED: Dizziness(7, 9, 10) Drowsiness(4) General Weakness(4) Headache(2, 5, 6, 7, 9, 10) Pruritus(4) |

3. Methods of Using Online Medication Profile

The following steps exemplify how a patient may access his or her medical profile.

1. Access the website of the medical profile provider, such as www.maxwellmedical.com.

2. Enter the patient identification number and pass code in order to access the medical information. Subsequent to validation and approval of the patient's identification number and pass code, the patient's access to the medical information is logged. The patient is provided with an on-screen medication profile report. The medication profile report is also available in a printed format.

While a health care provider can use the patient's identification number and password to access the information to the patient, provided the patient gives them the identification number and password, a registered health care provider can obtain a more detailed report. A registered health care provider may also use the on-line medication profile. The health care provider must register with the medication profile provider in order to obtain an identification number and pass code. The health care provider uses the following steps to access the patient's profile.

1. Access the website of the medical profile provider, such as www.maxwellmedical.com.

2. Enter the health care provider identification number and pass code. The website validates and approves the identification number and pass code.

3. Enter a patient's social security number and date of birth in order to retrieve medical information or the patient's identification and password. The health care provider obtains a complete medication profile report in an on-screen display. The report is also available in a printed format. The health care provider then uses the information within the medication profile report for medical decision purposes.

What is claimed is:

1. A medical information processing method, comprising:
providing a data processing system accessible to a plurality of users via a communications network, the data processing system including a computer program effective to execute the steps of
(a) receiving at the data processing system and from a remote user location via the communications network a request for medical information associated with a patient;
(b) obtaining medication specific data representing physical conditions associated with the patient, the medication specific data comprising
  names of one or more medications of a patient as recorded by a medical history of the patient, as determined from one or more sources independent of the patient, the medications further comprising discontinued medications and current medications, and
  names of all physical conditions that are medically known to be treated by the medications, as determined from one or more predetermined information databases;
(c) identifying within the data processing system one or more probable disease/drug contra-indications based upon relationships between the one or more medications and the physical conditions, said contra-indications further identified as significant or non-significant;
(d) generating within the data processing system a list of physical conditions comprising only the physical conditions that are not associated with said contra-indications and the physical conditions that are associated with said non-significant contra-indications;
(e) identifying within the data processing system consequential information associated with the medications currently in use by the patient, said consequential information including significant and non-significant side effects that are probable, significant and non-significant drug-drug interactions that are probable; and therapeutic classes;
(f) outputting from the data processing system to a remote user location via the communications network the generated list of physical conditions and the identified consequential information.

2. The method of claim 1, further comprising the step of:
(g) assigning the user an identification code; assigning the user a pass code; and upon entry of an identification code and pass code, comparing the entered identification code and the pass code to the assigned identification code and the assigned pass code to authorize access to the output physical conditions and consequential information.

3. The method of claim 1, wherein, in step (b) the medication specific data further comprises at least one of the items of data selected from the following group:
   an administration dose of the medication;
   a name of a health care provider that prescribed the medication;
   an original date of a prescription for the medication;
   a date of exhaustion of the prescription for the medication;
   a set of instructions for administering the medication; and
   compliance information for the medication.

4. The method of claim 1, wherein:
   in step (b) the medication specific data includes information indicative of patient usage of prescribed medications; and
   in step (e) the consequential information includes information regarding the indicated patient usage of prescribed medications.

5. The method of claim 2, wherein:
   step (g) includes enabling a selected class of users to access less than all of the consequential information.

* * * * *